United States Patent [19]

Fukumoto et al.

[11] Patent Number: 5,481,040
[45] Date of Patent: Jan. 2, 1996

[54] PROCESS FOR THE PREPARATION OF PHOSPHONIUM SALTS

[75] Inventors: Takehiko Fukumoto; Kazushi Hirokawa; Kurao Okada, all of Niigata, Japan

[73] Assignee: Shin-Etsu Chemical Co., Ltd., Tokyo, Japan

[21] Appl. No.: 412,912

[22] Filed: Mar. 29, 1995

[51] Int. Cl.⁶ ........................................... C07F 9/02
[52] U.S. Cl. ........................................................ 568/9
[58] Field of Search ...................................... 568/9

[56] References Cited

U.S. PATENT DOCUMENTS

| | | | |
|---|---|---|---|
| 4,122,123 | 10/1978 | Hestermann et al. | 260/606.5 F |
| 4,264,593 | 4/1981 | Sukman | 424/198 |
| 4,482,751 | 11/1984 | Javdani et al. | 568/626 |
| 5,055,619 | 10/1991 | Gitzel et al. | 568/2 |
| 5,250,736 | 10/1993 | Micklethwaite et al. | 568/8 |

*Primary Examiner*—Porfirio Nazario-Gonzales
*Attorney, Agent, or Firm*—Arnold, White & Durkee

[57] ABSTRACT

A process for the preparation of phosphonium salts by the use of chlorides, which is useful in the course of synthesis of olefin compounds by the Wittig reaction, and which comprises reacting a phosphine compound of the general formula $$R^1{}_3P$$

wherein $R^1$ is a phenyl group or a straight-chain alkyl group having 2 to 8 carbon atoms, with a primary or secondary chloride of the general formula $$\begin{array}{c} R^2 \\ \phantom{xx}\diagdown \\ \phantom{xxxx}CHCl \\ \phantom{xx}\diagup \\ R^3 \end{array}$$

wherein $R^2$ and $R^3$ are hydrocarbon radicals, in a solvent selected from the group consisting of N,N-dimethylformamide, N,N-dimethylacetamide and N,N-1,3-dimethyl-2-imidazolidinone, and in the presence of an alkali metal salt of the general formula MBr or MI.

2 Claims, No Drawings

PROCESS FOR THE PREPARATION OF PHOSPHONIUM SALTS

FIELD OF THE INVENTION AND RELATED ART STATEMENT

This invention relates to a process for the preparation of phosphonium salts which are indispensable in the course of the synthesis by the Wittig reaction of olefin compounds present in various chemical products, agricultural chemicals, medicines, perfumes, physiologically active substances and intermediates thereof.

The Wittig reaction, in which a phosphonium salt is deprotonated by a base to form a phosphorane and this is reacted with an aldehyde or ketone to form a vinyl group in the latter with specificity and positional selectivity, is one of the excellent methods for the synthesis of olefins and provides a very effective means in the field of organic synthetic chemistry. Many reports have already been made on the Wittig reaction, and the process commonly employed therein to prepare phosphonium salts involves reacting a phosphine, typified by triphenylphosphine, with a primary or secondary halide under heated conditions, in the presence or absence of a solvent [see Org. React., 14, 270 (1965); and New Course of Experimental Chemistry, Vol.14, "Synthesis and Reactions of Organic Compounds (I)", Maruzen, p.224 (1977)].

Generally, phosphonium salts are synthesized from a phosphine and a highly reactive primary or secondary halide by an $S_N 2$ type reaction. Accordingly, the reaction rate varies with the type of halogen, and the decreasing order thereof is as follows: I>Br>Cl. Although numerous examples of the reaction have been reported up to now, most of them use bromides or iodides because of their high reaction rates [see Org. React., 14, 388 (1965)]. Moreover, the reaction also depends on the temperature and the reaction time, so that a high degree of conversion can be achieved by carrying out the reaction at a high temperature for a long period of time.

On the other hand, in order to obtain a desired olefin of high purity by the Wittig reaction, it is very important to purify the halide used in the preceding step. While distillation is the purification technique most frequently used for industrial purposes, the boiling points of halides become lower in the following order: I>Br>Cl. Accordingly, when viewed from the standpoint of distillation under heated conditions, chlorides are the best choice because of their high thermal stability. In contrast, iodides and bromides are poor in thermal stability and involve a great risk of being deteriorated during distillation, thus requiring extreme care. Especially in the case of halides having another functional group in the molecule, not a few of them seem unable to withstand distillation on an industrial scale.

SUMMARY OF THE INVENTION

As described above, the use of a chloride is beneficial for purposes of distillation because of its low boiling points. On the other hand, it is disadvantageous in that its rate of conversion to a phosphonium salt is low.

In order to overcome this disadvantage, its rate of formation of a phosphonium salt can be increased to some degree by raising the reaction temperature. However, the risk of deteriorating the chloride is increased at the same time. Thus, an efficient process for preparing phosphonium salts by use of chlorides is being sought.

The present inventors made intensive investigations for the purpose of solving this problem. As a result, it has been discovered that phosphonium salts can very satisfactorily be prepared under mild conditions by reacting a phosphine compound of the general formula

wherein $R^1$ is a phenyl group or a straight-chain alkyl group having 2 to 8 carbon atoms, with a primary or secondary chloride of the general formula

wherein $R^2$ is a hydrogen atom, an alkyl group, a hydrocarbon group having an unsaturated bond, or a hydrocarbon radical having a hydroxyl group protected by a protecting group in the molecule, and $R^3$ is a hydrogen atom, a saturated hydrocarbon radical or an unsaturated hydrocarbon radical, in a solvent selected from the group consisting of N,N-dimethylformamide, N,N-dimethylacetamide and N,N-1,3-dimethyl-2-imidazolidinone, and in the presence of an alkali metal salt of the general formula

or

wherein M is Li, Na or K. The present invention has been completed on the basis of this discovery.

According to the present invention, it is possible to prepare phosphonium salts efficiently by the use of chlorides.

If an attempt is made to prepare a phosphonium salt directly from a chloride as in the prior art, it will be difficult to bring the reaction to completion. Thus, unreacted chloride will remain as a result of the incomplete reaction. Since this remaining chloride reacts with the base used during the Wittig reaction, a purification procedure for removing unreacted chloride from the phosphonium salt is indispensable.

The present invention can minimize the amount of the remaining unreacted chloride and thereby eliminate the necessity of a purification procedure for the removal of unreacted chloride, so that the reaction solution for the synthesis of a phosphonium salt can be used directly in the Wittig reaction.

Moreover, the reaction can be carried out in the copresence of another solvent (such as THF) favorable for the Wittig reaction.

Thus, the production system is freed from complexity.

Furthermore, it is also possible to recover the solvent from the reaction solution for the synthesis of a phosphonium salt in accordance with the present invention, purify the phosphonium salt according to common purification techniques such as recrystallization, and then subject it to the Wittig reaction in another solvent system.

DETAILED DESCRIPTION OF PREFERRED EMBODIMENTS

The present invention is characterized in that a halogen exchange reaction by an alkali metal salt and a phosphonium salt synthesis reaction are carried out in the same solvent. These reactions are shown below.

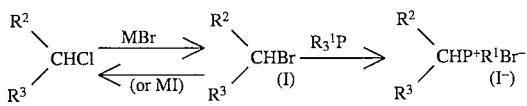

Solvents often used in halogen exchange reactions include acetone, 2-butanol, ethanol and N,N-dimethylformamide (hereinafter abbreviated as "DMF"). However, acetone, 2-butanol and ethanol are excluded in view of the fact that they cannot be used in the Wittig reaction.

On the other hand, solvents often used in phosphonium salt synthesis reactions include acetonitrile, DMF, toluene, benzene and the like [Liebig Ann. Chem., 1705–1720 (1981)].

As a result of investigation on solvents suitable for the purpose of carrying out the above-described two reactions in the same solvent, there were chosen DMF, N,N-dimethylacetamide (hereinafter abbreviated as "DMAC") represented by the chemical formula

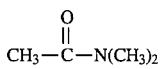

and N,N-1,3-dimethyl-2-imidazolidinone (hereinafter abbreviated as "DMI") represented by the chemical formula

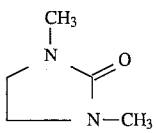

The above-defined solvent is used in an amount of 50 to 500 g per mole of the chloride. If its amount is less than 50 g, the halogen exchange reaction will be retarded. If its amount is greater than 500 g, no additional improvement in reaction rate will be achieved and, therefore, it is unnecessary to use the solvent in excess. The solubility of the alkali metal salt may vary according to the amount of solvent used, causing a change in the rate of the halogen exchange reaction. Accordingly, in order to enhance the reaction rate, it is desirable to use the solvent in a more than sufficient amount. Preferably, the solvent is used in an amount of 200 to 500 g per mole of the chloride.

Specific examples of the phosphine compound represented by the general formula $R^1_3P$ include triphenylphosphine that is readily available and is commonly used, particularly in the Wittig reaction. In addition, triethylphosphine, tri-n-propylphosphine, tri-n-butylphosphine, tri-n-hexylphosphine, tri-n-octylphosphine and the like can also be used in the present invention. The phosphine compound is used in an amount of 1.0 to 2.0 moles per mole of the chloride. If its amount is less than 1.0 mole, the phosphine compound is stoichiometrically insufficient and a part of the chloride will remain unreacted. If its amount is greater than 2.0 moles, the phosphine compound is present in excess and makes it difficult to isolate the olefin after the Wittig reaction.

Examples of useful primary chlorides include 8-(tetrahydro-2-pyranyloxy)octyl chloride, 9-trimethylsilyloxynonyl chloride, 10-acetoxydecyl chloride, 4-heptenyl chloride and 4-decenyl chloride.

Examples of useful secondary chlorides include 2-chlorohexane, 3-chloroheptane and 4-methyl-2-chlorohexane.

Specific examples of the alkali metal salt represented by the general formula MBr or MI include bromides such as NaBr, KBr and LiBr, and iodides such as NaI, KI and LiI. The alkali metal salt is used in an amount of 0.9 to 3.0 moles per mole of the chloride. If its amount is less than 0.9 mole, the rate of formation of the phosphonium salt will be reduced. If its amount is greater than 3.0 moles, no additional improvement in the rate of formation of the phosphonium salt will be achieved.

Generally, the halogen exchange reaction is reversible and the exchange will be incomplete when the salt resulting from the exchange reaction has high solubility.

However, since the resulting bromide or iodide is consumed by reacting with the phosphine compound to form a phosphonium salt, the equilibrium is shifted to the direction which promotes the exchange reaction.

Accordingly, although the halogen exchange reaction is reversible, the alkali metal salt need not be used in large excess. Generally, iodides give a higher reaction rate than bromides.

However, a lithium salt (i.e., LiBr or LiI) is used, care must be taken not to carry out the Wittig reaction directly in the presence of the lithium salt because this may reduce the selectivity to cis-isomers.

Where an alkyl chloride is used, the reaction temperature and the reaction time are usually in the range of 40° to 200° C. and 5 to 30 hours, respectively. Where the chloride has an unsaturated bond, the reaction temperature and the reaction time are usually in the range of 60° to 120° C. and about 10 to 20 hours, respectively. Under these conditions, an isomerization may occur during the reaction. Where the chloride has a hydroxyl group protected by a protecting group, care must be taken not to raise the reaction temperature excessively because such high temperatures may cause the protecting group to be removed. However, if the reaction is carried out at a temperature of 60° to 100° C. for a period of 10 to 30 hours, the reaction will proceed to a degree of conversion of about 95% or greater. Where the chloride has a low boiling point, the reaction may be carried out under pressure in an autoclave.

EXAMPLES

The present invention is further illustrated by the following examples. However, these examples are not to be construed to limit the scope of the invention.

Reaction Conditions

A reactor was charged with 26.2 g (0.1 mole; 1 mole per mole of the chloride) of triphenylphosphine, 30 g (300 g per mole of the chloride) of a solvent, and a given amount of an alkali metal salt. After the addition of 0.1 mole of a chloride, the resulting reaction mixture was reacted at a predetermined temperature under an atmosphere of nitrogen gas for a predetermined time. Thereafter, the reaction mixture was cooled to room temperature, followed by the addition of 10 g of n-octyl alcohol. Using this n-octyl alcohol as internal standard, the reaction mixture was analyzed by gas chromatography (GC) and the rate of decrease of the chloride based on the n-octyl alcohol was calculated according to the equation given below. The progress of the reaction was estimated by regarding the rate of decrease of the chloride as its degree of conversion.

Degree of conversion (percent decrease of chloride)

$$=\{(C\times B\div A)-D\}\div (C\times B\div A)\times 100$$

where A: GC(%) of n-octyl alcohol before the reaction.
B: GC(%) of the chloride before the reaction.
C: GC(%) of n-octyl alcohol after the reaction.
D: GC(%) of the chloride after the reaction.

1) Preparation of n-decyltriphenylphosphonium bromide

As the alkali metal salt, there was used 20.4 g (2.1 moles per mole of the chloride) of NaBr (Examples 1–4 and Comparative Examples 1–3), 23.6 g (2.1 moles per mole of the chloride) of KBr (Example 5) or 17.2 g (2.1 moles per mole of the chloride) of LiBr (Example 6).

As the chloride, there was used 17.7 g of $CH_3(CH_2)_9Cl$.

The reaction conditions and the results are shown in Table 1.

TABLE 1

| | Alkali metal salt | Solvent | Reaction temperature (°C.) | Time (hr) | Rate of decrease of chloride (%) |
|---|---|---|---|---|---|
| Example 1 | NaBr | DMF | 100 | 20 | 99 |
| Example 2 | NaBr | DMF | 80 | 20 | 96 |
| Example 3 | NaBr | DMI | 100 | 20 | 97 |
| Example 4 | NaBr | DMAC | 100 | 20 | 98 |
| Example 5 | KBr | DMF | 100 | 15 | 99 |
| Example 6 | LiBr | DMF | 100 | 20 | 95 |
| Comparative Example 1 | NaBr | Toluene | 100 | 20 | 24 |
| Comparative Example 2 | NaBr | $CH_3CN$ | 81 | 20 | 30 |
| Comparative Example 3 | NaBr | THF | 68 | 20 | 11 |

2) Preparation of 8-(tetrahydro-2-pyranyloxy)octyltriphenylphosphonium bromide

As the alkali metal salt, there was used 20.4 g (2.0 moles per mole of the chloride) of NaBr (Examples 7–9 and Comparative Examples 4–5) or 23.6 g (2.0 moles per mole of the chloride) of KBr (Example 10).

As the chloride, there was used 29.1 g of the compound represented by the following chemical formula:

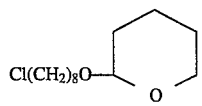

The reaction conditions and the results are shown in Table 2.

TABLE 2

| | Alkali metal salt | Solvent | Reaction temperature (°C.) | Time (hr) | Rate of decrease of chloride (%) |
|---|---|---|---|---|---|
| Example 7 | NaBr | DMF | 90 | 20 | 96 |
| Example 8 | NaBr | DMAC | 90 | 20 | 91 |
| Example 9 | NaBr | DMI | 90 | 20 | 96 |
| Example 10 | KBr | DMF | 90 | 20 | 97 |
| Comparative Example 4 | NaBr | $CH_3CN$ | 81 | 20 | 19 |
| Comparative Example 5 | NaBr | Benzene | 79 | 20 | 13 |

TABLE 2-continued

| | Alkali metal salt | Solvent | Reaction temperature (°C.) | Time (hr) | Rate of decrease of chloride (%) |
|---|---|---|---|---|---|
| Example 5 | | | | | |

3) Preparation of Z-4-octenyltriphenylphosphonium bromide

As the alkali metal salt, there was used 15.3 g (1.5 moles per mole of the chloride) of NaBr (Examples 11–13 and Comparative Example 6) or 17.2 g (2.0 moles per mole of the chloride) of LiBr (Example 14).

As the chloride, there was used 14.6 g of the compound represented by the following chemical formula:

$$CH_3(CH_2)_2CH=CH(CH_2)_3Cl$$

The reaction conditions and the results are shown in Table 3.

TABLE 3

| | Alkali metal salt | Solvent | Reaction temperature (°C.) | Time (hr) | Rate of decrease of chloride (%) |
|---|---|---|---|---|---|
| Example 11 | NaBr | DMF | 80 | 15 | 90 |
| Example 12 | NaBr | DMAC | 80 | 15 | 88 |
| Example 13 | NaBr | DMI | 80 | 16 | 88 |
| Example 14 | LiBr | DMF | 80 | 15 | 91 |
| Comparative Example 6 | NaBr | $CH_3CN$ | 80 | 16 | 16 |

4) Preparation of 9-(trimethylsilyloxy)nonyltriphenylphosphonium bromide

As the alkali metal salt, there was used 15.3 g (1.5 moles per mole of the chloride) of NaBr (Examples 15–17 and Comparative Example 7).

As the chloride, there was used 25.0 g of the compound represented by the following chemical formula:

$$Cl(CH_2)_9OSi(CH_3)_3$$

The reaction conditions and the results are shown in Table 4.

TABLE 4

| | Alkali metal salt | Solvent | Reaction temperature (°C.) | Time (hr) | Rate of decrease of chloride (%) |
|---|---|---|---|---|---|
| Example 15 | NaBr | DMF | 100 | 20 | 99 |
| Example 16 | NaBr | DMF | 70 | 20 | 87 |
| Example 17 | NaBr | DMI | 100 | 20 | 97 |
| Comparative Example | NaBr | $CH_3CN$ | 81 | 20 | 13 |

5) Preparation of Z-4-decenyltriphenylphosphonium iodide

As the alkali metal salt, there was used 18.0 g (1.2 moles per mole of the chloride) of NaI (Example 18), 23.0 g (1.53 moles per mole of the chloride) of NaI (Example 19, Comparative Example 8) or 21.6 g (1.3 moles per mole of the chloride) of KI (Example 20).

As the chloride, there was used 17.5 g of the compound represented by the following chemical formula:

$$CH_3(CH_2)_4CH=CH(CH_2)_3Cl$$

The reaction conditions and the results are shown in Table 5.

TABLE 5

| | Alkali metal salt | Solvent | Reaction temperature (°C.) | Time (hr) | Rate of decrease of chloride (%) |
|---|---|---|---|---|---|
| Example 18 | NaI | DMF | 90 | 20 | 94 |
| Example 19 | NaI | DMF | 90 | 20 | 98 |
| Example 20 | KI | DMF | 90 | 20 | 98 |
| Comparative Example 8 | NaI | Toluene | 90 | 20 | 17 |

APPLICATION EXAMPLES (1) Synthesis of Z-9-tricosene [the sex pheromone of the housefly (Musca domestica)]

A reactor was charged with 131 g of triphenylphosphine, 60 g of DMF, 102 g of NaBr and 110 g (0.47 mole) of 1-chlorotetradecane, and this mixture was stirred at 120° C. under an atmosphere of $N_2$ for 20 hours. Then, the reactor was evacuated to 30 mmHg until almost all of the DMF was recovered. After 1 liter of THF was added to the residue, 320 milliliters of a 15% solution of n-butyllithium in hexane was added dropwise thereto at 0°–10° C. Then, the resulting mixture was cooled to −30° C. and 70 g of nonyl aldehyde was added dropwise thereto over a period of an hour. Upon completion of the addition, the reaction was stopped by the addition of 10 milliliters of water and the THF was recovered under reduced pressure. 400 milliliters each of n-hexane and pure water were added to the residue and the resulting insoluble triphenylphosphine oxide was separated by filtration. The organic layer thus obtained was washed with 500 milliliters of pure water. After the n-hexane was removed, the residue was distilled under reduced pressure to obtain 96.6 g of 9-tricosene (composed of 88% of the Z-isomer and 12% of the E-isomer). Its boiling point was 195°–199° C. at 2 mmHg.

(2) Synthesis of Z-E-9,11-tetradecadienyl acetate [the sex pheromone of an armyform (Spodoptera litura)]

A reactor was charged with 131 g of triphenylphosphine, 200 g of DMF, 102 g of NaBr and 125 g of 9-(trimethylsilyloxy)-nonyl- 1-chloride, and this mixture was stirred at 100° C. under an atmosphere of $N_2$ for 20 hours. After the addition of 1 liter of THF, the mixture was cooled to 0° C. and 56 g of tert-butoxypotassium was added thereto, followed by stirring for an hour. Then, 43 g of E-2-pentenal was added dropwise thereto at −20° C. Upon completion of the addition, the THF was removed under reduced pressure. 400 milliliters each of pure water and n-hexane were added to the residue and the resulting insoluble triphenylphosphine oxide was separated by filtration. The hexane layer thus obtained was mixed with 60 g of triethylamine and acetylated by adding 47 g of acetyl chloride dropwise thereto. Upon completion of the addition, the reaction mixture was washed twice with 500 milliliters of pure water. After the n-hexane was removed from the organic layer, the residue was distilled under reduced pressure to obtain 151 g of 9,11-tetradecenyl acetate (composed of 87% of the Z-E-isomer and 13% of the E-E-isomer). Its boiling point was 143°–147° C. at 3 mmHg.

We claim:

1. A process for the preparation of phosphonium salts which comprises reacting a phosphine compound of the general formula $$R^1{}_3P$$

wherein $R^1$ is a phenyl group or a straight-chain alkyl group having 2 to 8 carbon atoms, with a primary or secondary chloride of the general formula $$\begin{array}{c} R^2 \\ \phantom{R^2}\diagdown \\ \phantom{R^2R^2}CHCl \\ \phantom{R^2}\diagup \\ R^3 \end{array}$$

wherein $R^2$ is a hydrogen atom, an alkyl group, a hydrocarbon group having an unsaturated bond, or a hydrocarbon radical having a hydroxyl group protected by a protecting group in the molecule, and $R^3$ is a hydrogen atom, a saturated hydrocarbon radical or an unsaturated hydrocarbon radical, in one or more solvent selected from the group consisting of N,N-dimethylformamide, N,N-dimethylacetamide and N,N-1,3-dimethyl-2-imidazolidinone, and in the presence of an alkali metal salt of the general formula $$MBr$$

or $$MI$$

wherein M is Li, Na or K.

2. A process for the preparation of phosphonium salts as claimed in claim 1 wherein the phosphine compound is triphenylphosphine.

* * * * *